United States Patent
Asakawa et al.

(10) Patent No.: US 8,265,880 B2
(45) Date of Patent: Sep. 11, 2012

(54) GENE EXPRESSION LEVEL ANALYZING METHOD, GENE EXPRESSION LEVEL ANLAYZING PROGRAM, AND GENE EXPRESSION LEVEL ANALYZING DEVICE

(75) Inventors: Takeshi Asakawa, Chiba (JP); Naoya Sazuka, Tokyo (JP); Tetsuya Shiraishi, Tokyo (JP)

(73) Assignee: Sony Corporation, Tokyo (JP)

( * ) Notice: Subject to any disclaimer, the term of this patent is extended or adjusted under 35 U.S.C. 154(b) by 616 days.

(21) Appl. No.: 12/496,029

(22) Filed: Jul. 1, 2009

(65) Prior Publication Data
US 2010/0009369 A1    Jan. 14, 2010

(30) Foreign Application Priority Data
Jul. 9, 2008    (JP) .................................. 2008-179255

(51) Int. Cl.
*G06F 19/00* (2011.01)
*G06F 15/00* (2006.01)
*G11C 17/00* (2006.01)
*C12Q 1/68* (2006.01)

(52) U.S. Cl. .................. 702/20; 365/94; 700/1; 435/6.1

(58) Field of Classification Search .................. None
See application file for complete search history.

(56) References Cited

OTHER PUBLICATIONS

Ido Amit et al.; A module of negative feedback regulators defines growth factor signaling; Nature Genetics; vol. 39; No. 4; Apr. 2007.

*Primary Examiner* — John S Brusca
(74) *Attorney, Agent, or Firm* — SNR Denton US LLP

(57) ABSTRACT

A gene expression level analyzing method includes the steps of: acquiring expression levels of a plurality of target genes in a target cell every measurement time; extracting a maximum expression level and a minimum expression level from the expression levels of the target genes every measurement time; calculating a correlation coefficient of a frequency distribution of the gene having the maximum expression level at each measurement time and a frequency distribution of the gene having the minimum expression level at each measurement time; and comparing the correlation coefficient with a threshold value of the correlation coefficient.

7 Claims, 16 Drawing Sheets

ENTIRE CONFIGURATION OF MEASUREMENT SYSTEM

HYBRIDIZATION IN NUCLEIC ACID TIP

FIG.5

|  | t₁ | t₂ | ··· | tₘ |
|---|---|---|---|---|
| GE₁ | 2 (GE1max) | 1.1 (GE1min) | ··· | 1.3 |
| GE₂ | 0.5 (GE2min) | 1.9 (GE2max) | ··· | 1.3 |
| GE₃ | 1.6 | 0.3 (GE3min) | ··· | 1.7 (GE3max) |
| ⋮ | ⋮ | ⋮ | ⋮ | ⋮ |
| GEₙ | 0.2 (GEnmin) | 0.8 (GEnmax) | ··· | 0.5 |

EXTRACTION OF MAXIMUM AND MINIMUM EXPRESSION LEVELS IN EACH GENE

NUMBER OF PROBES:16896

CORRELATION COEFFICIENT OF A AND B:0.698

TEST RESULT 1

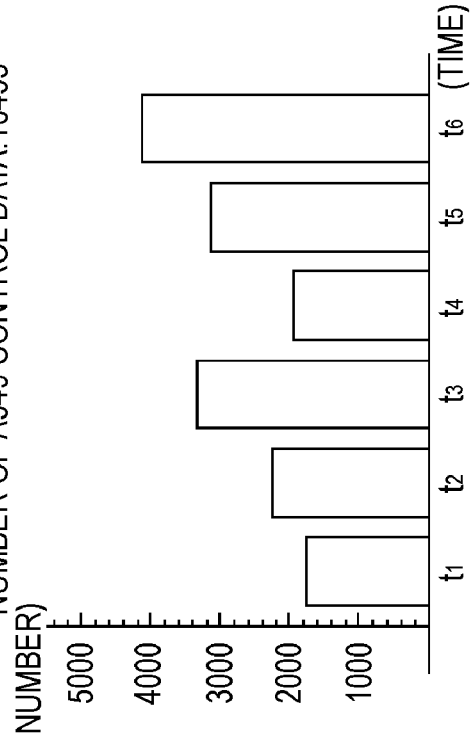
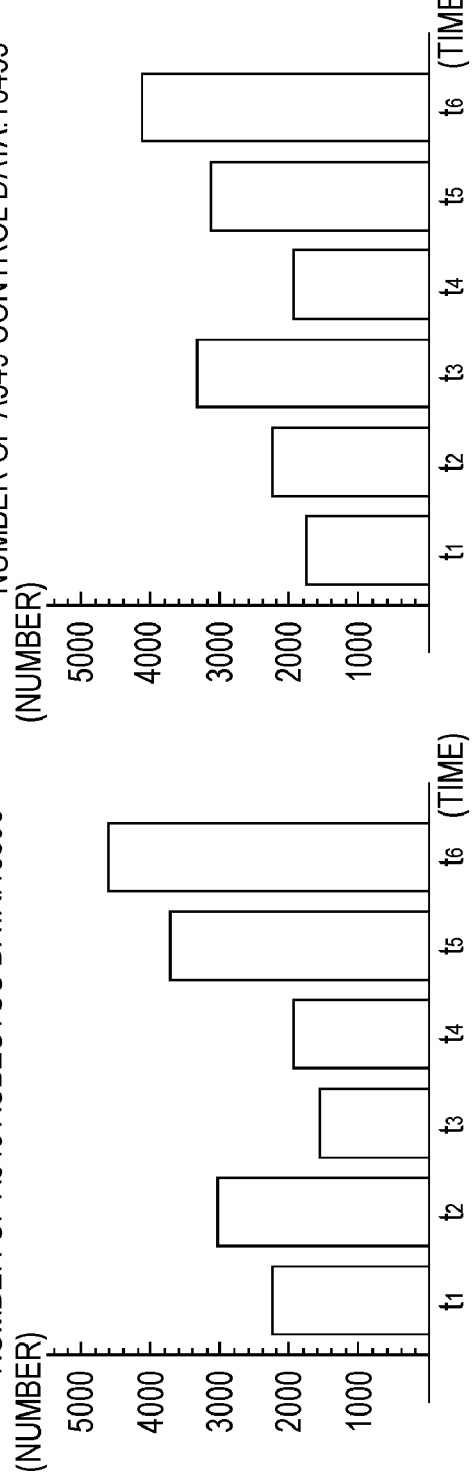
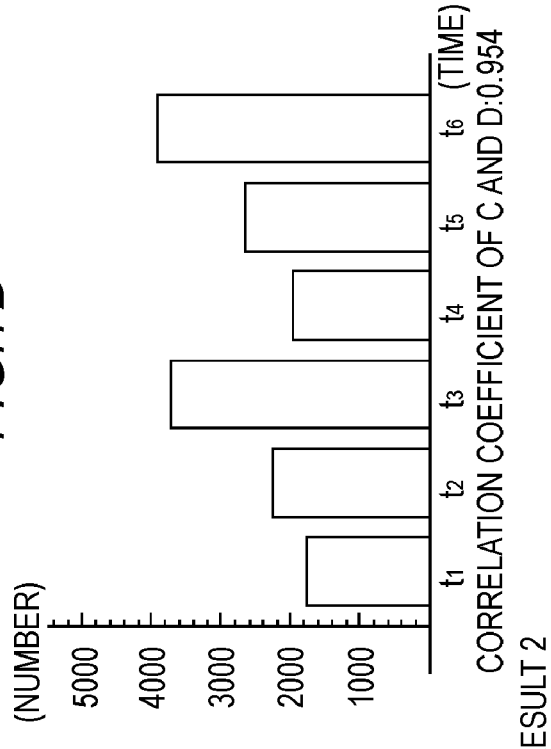
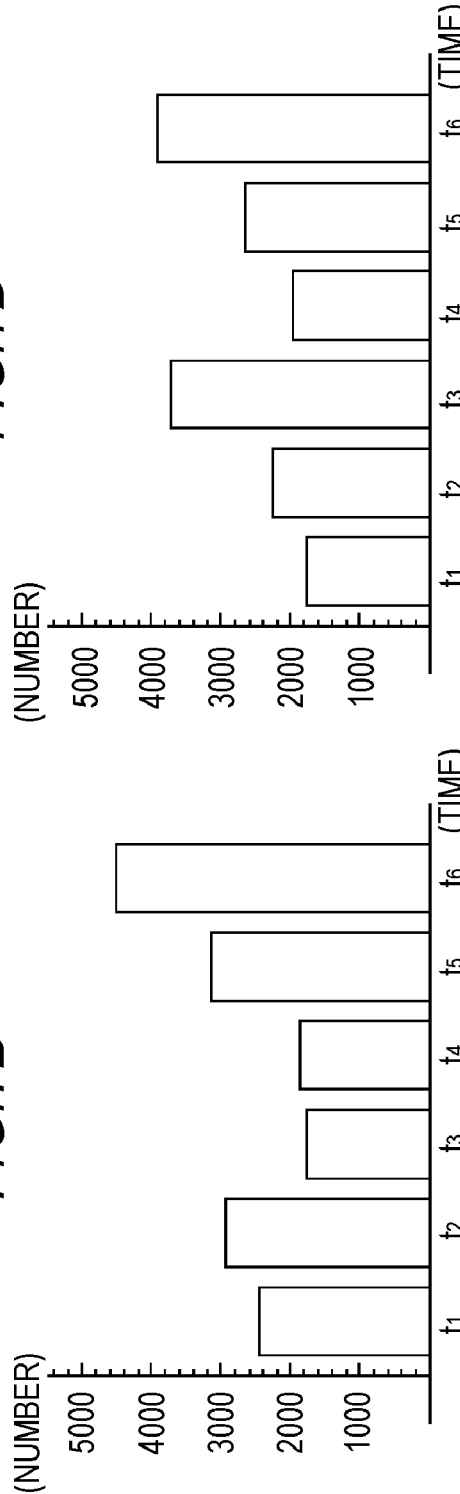

TEST RESULT 3

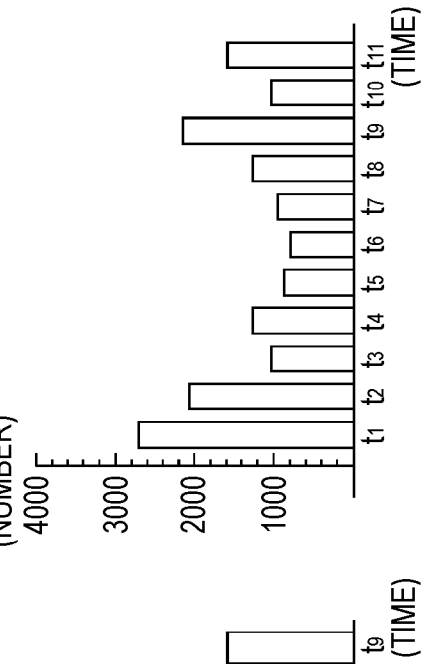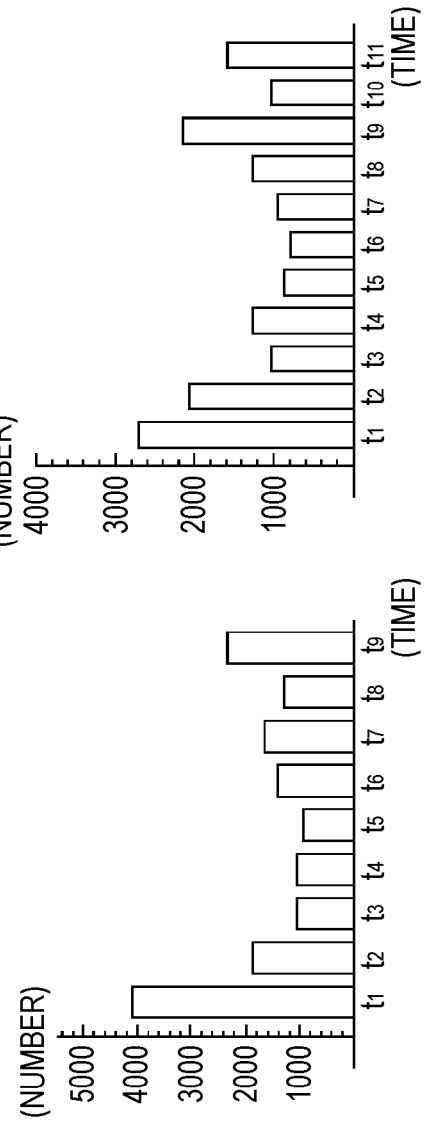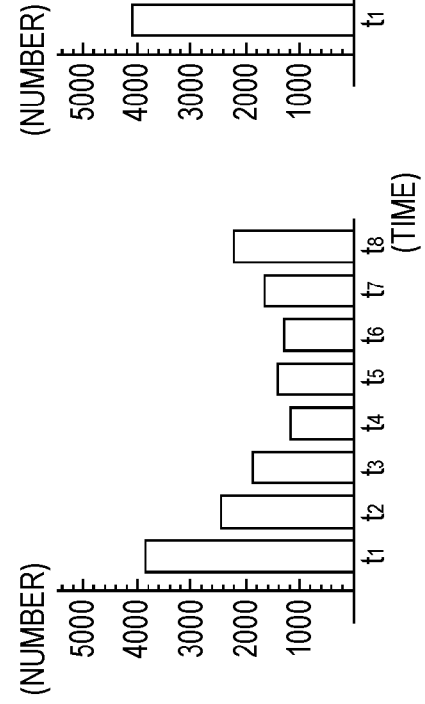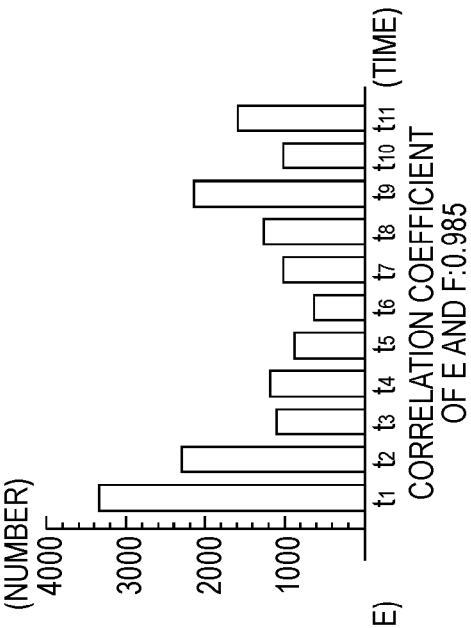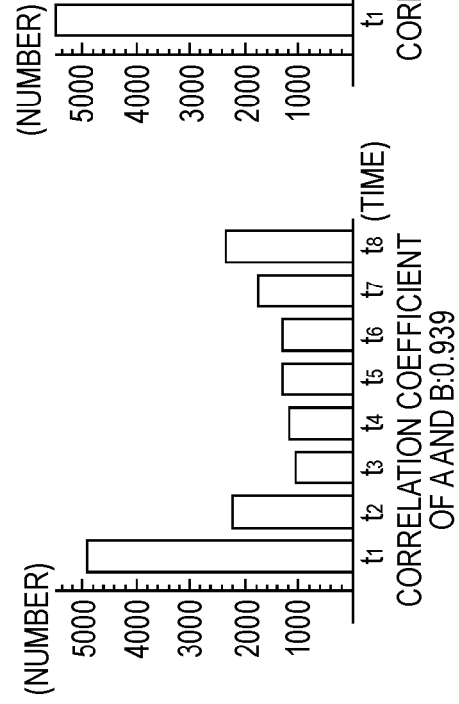

FLOW OF GENE EXPRESSION LEVEL ANALYZING PROCESS

FIG.11A

|     | t₁  | t₂  | ... | tₘ  |
|-----|-----|-----|-----|-----|
| GE₁ | 2   | 1.1 | ... | 1.3 |
| GE₂ | 0.5 | 1.9 | ... | 1.3 |
| GE₃ | 1.6 | 0.3 | ... | 1.7 |
| ⋮   | ⋮   | ⋮   |     | ⋮   |
| GEₙ | 0.2 | 0.5 | ... | 0.8 |

FIG.11B

|     | t₁  | t₂   | ... | tₘ   |
|-----|-----|------|-----|------|
| GE₁ | 1   | 0.55 | ... | 0.65 |
| GE₂ | 1   | 3.8  | ... | 2.6  |
| GE₃ | 1   | 0.19 | ... | 1.06 |
| ⋮   | ⋮   | ⋮    |     | ⋮    |
| GEₙ | 1   | 2.5  | ... | 4    |

CONVERSION OF EXPRESSION LEVEL OF EACH GENE INTO RATIO TO REFERENCE OF EXPRESSION LEVEL OF EACH GENE

FIG.12A

|  | $t_1$ | $t_2$ | ... | $t_m$ |
|---|---|---|---|---|
| $GE_1$ | 1 | 0.55 | ... | 0.65 |
| $GE_2$ | 1 | 3.8 | ... | 2.6 |
| $GE_3$ | 1 | 0.19 | ... | 1.06 |
| ⋮ | ⋮ | ⋮ | ⋮ | ⋮ |
| $GE_n$ | 1 | 2.5 | ... | 4 |

FIG.12B

|  | $t_1$ | $t_2$ | ... | $t_m$ |
|---|---|---|---|---|
| $GE_1$ | 1 | 0.55 | ... | 0.65 |
| $GE_2$ | 1 | 3.8 | ... | 2.6 |
| $GE_3$ | 1 | 0.19 | ... | 1.06 |
| ⋮ | ⋮ | ⋮ | ⋮ | ⋮ |
| $GE_n$ | 1 | 2.5 | ... | 4 |

EXTRACTION OF MAXIMUM AND MINIMUM
EXPRESSION LEVEL RATIOS OF EACH GENE

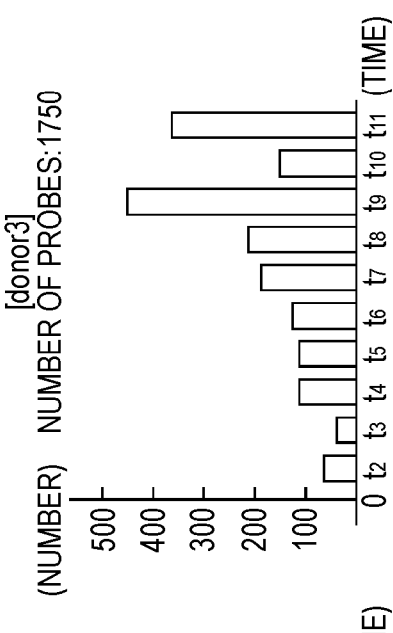
FIG.13A [donor1] NUMBER OF PROBES:2352
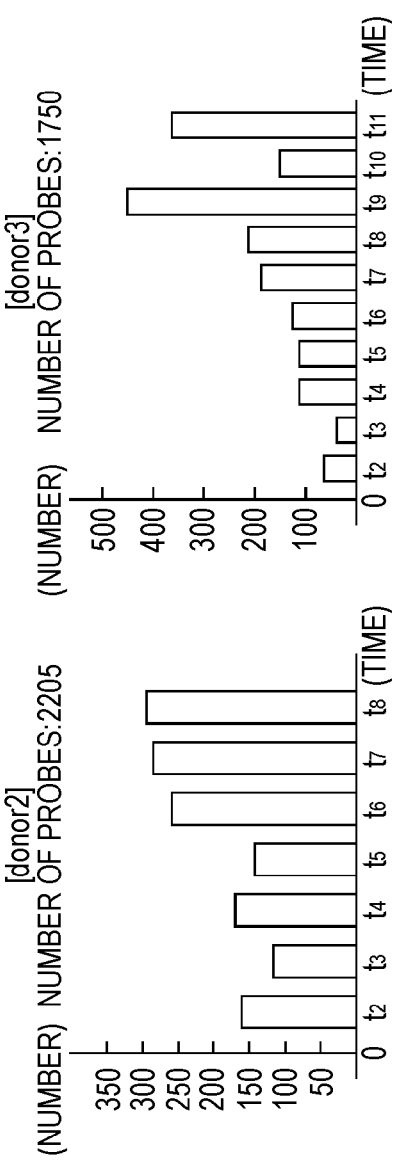
FIG.13B NUMBER OF PROBES:1939
CORRELATION COEFFICIENT OF A AND B:0.965
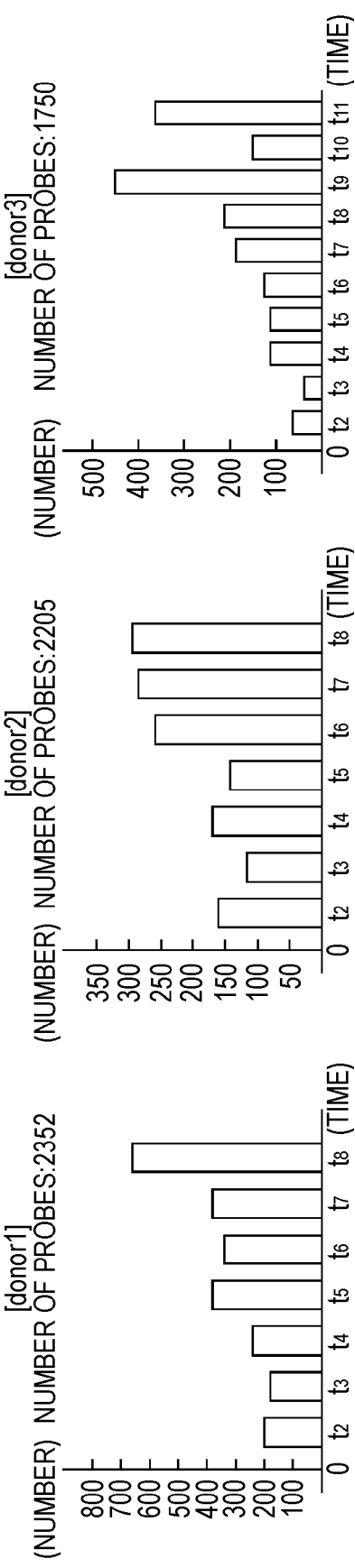
FIG.13C [donor2] NUMBER OF PROBES:2205
FIG.13D NUMBER OF PROBES:1851
CORRELATION COEFFICIENT OF C AND D:0.992
TEST RESULT 5
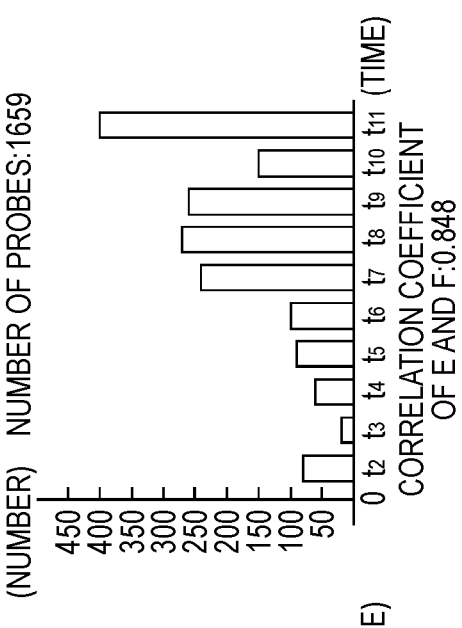
FIG.13E [donor3] NUMBER OF PROBES:1750
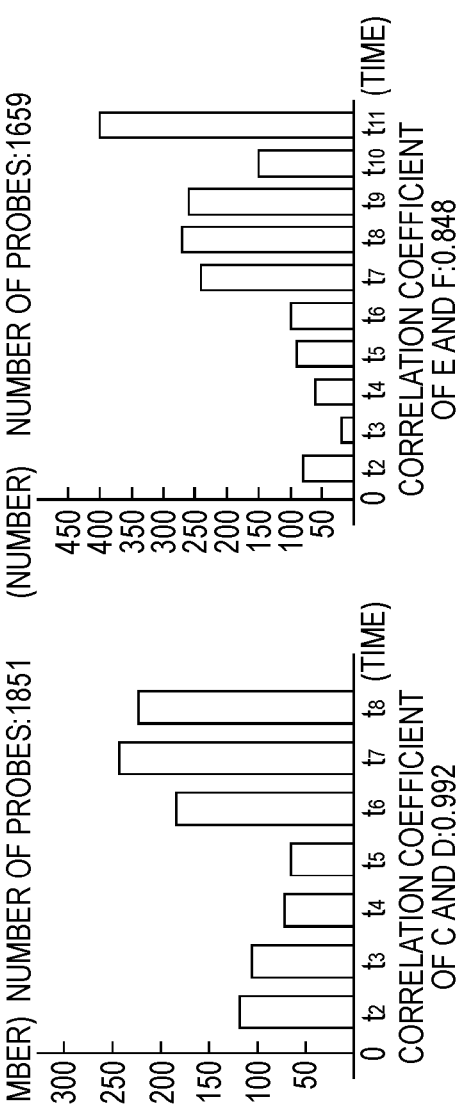
FIG.13F NUMBER OF PROBES:1659
CORRELATION COEFFICIENT OF E AND F:0.848
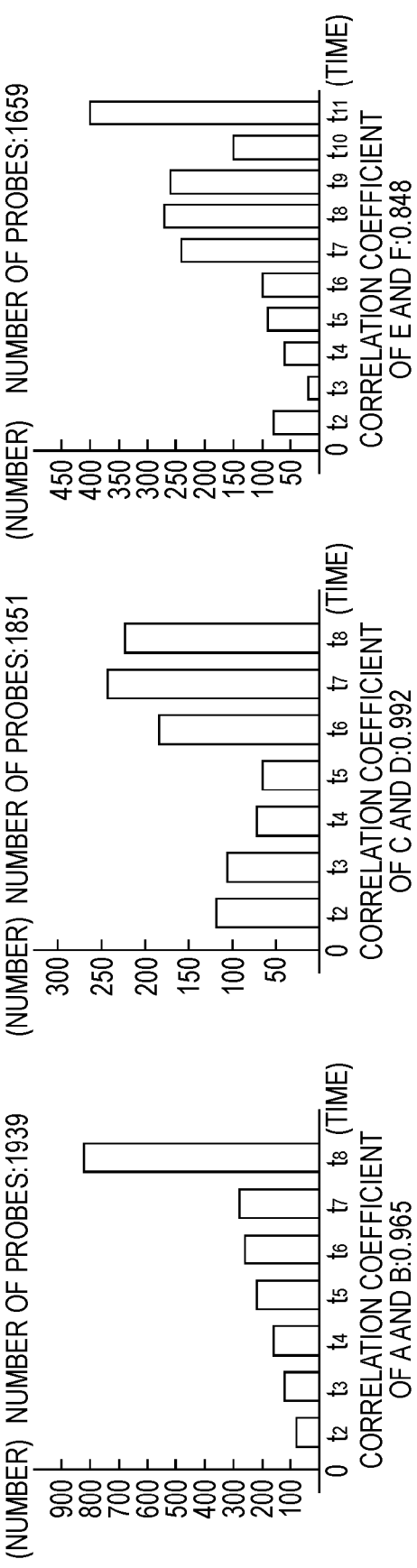

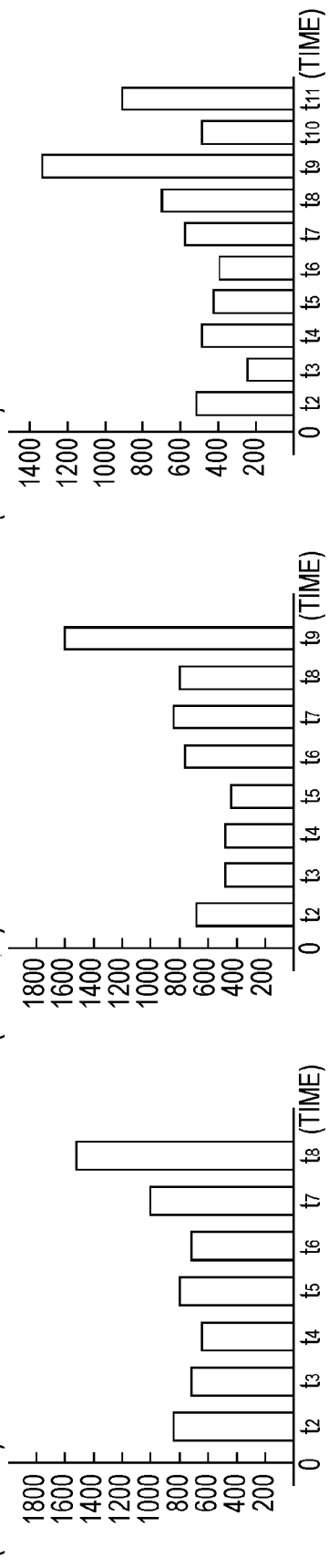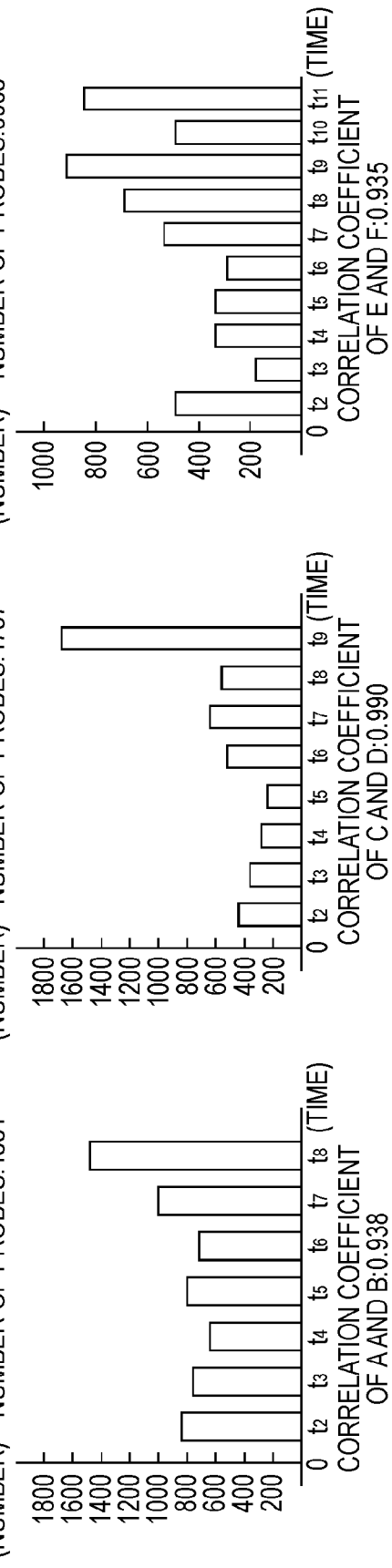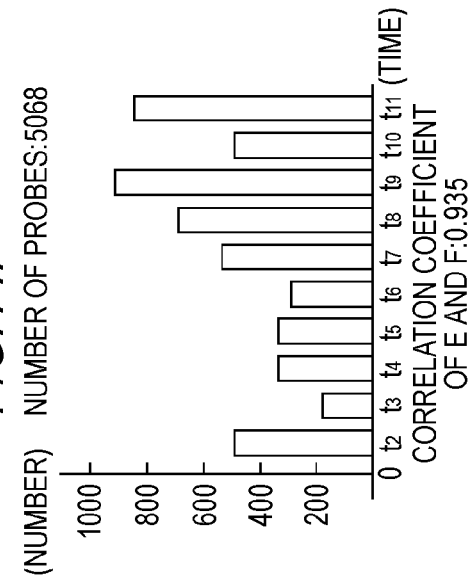

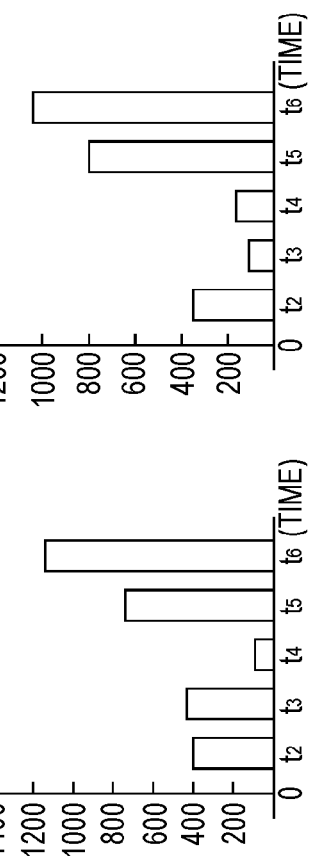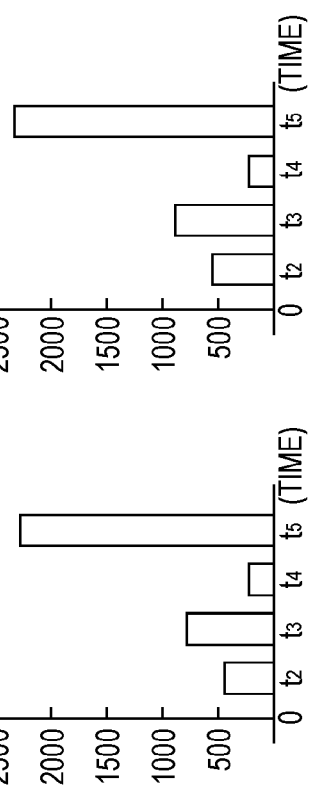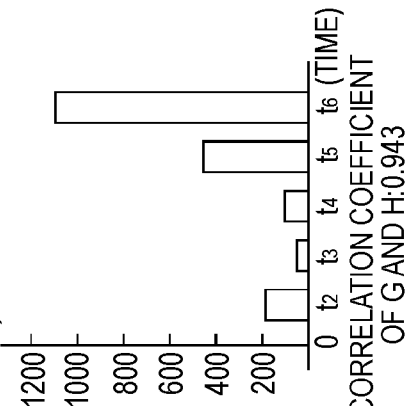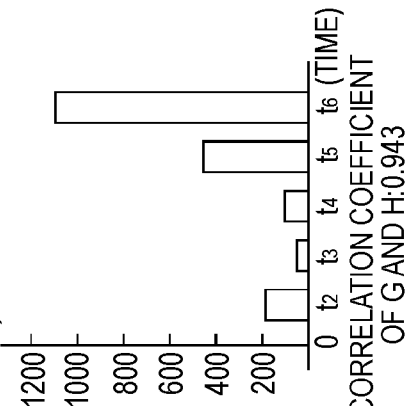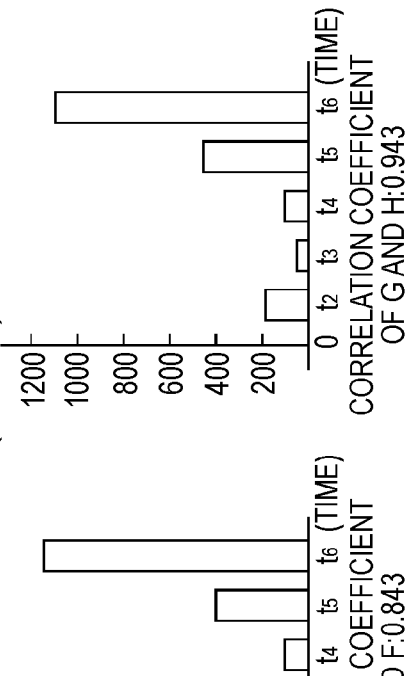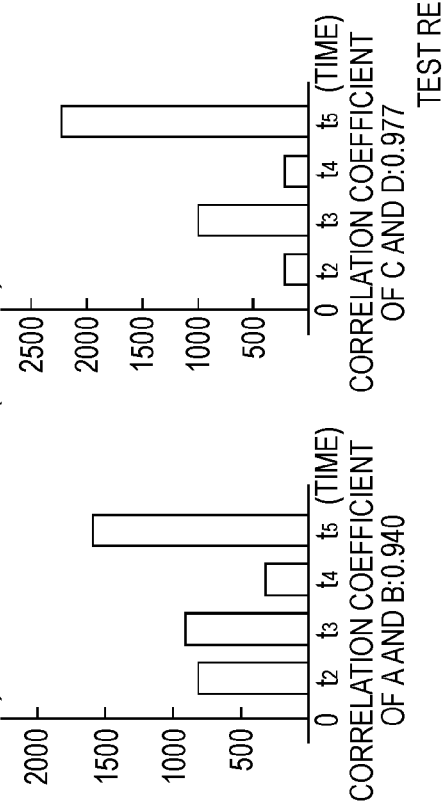

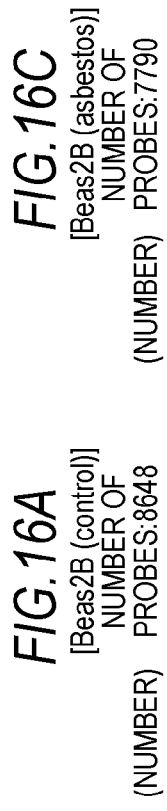
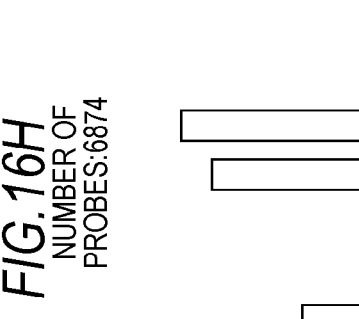
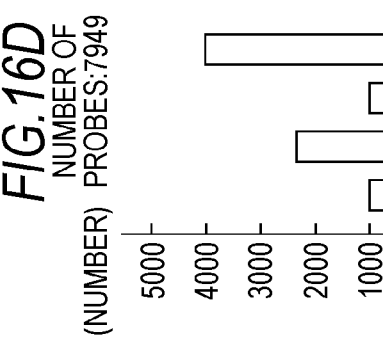
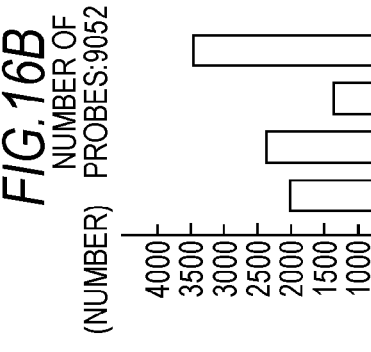
TEST RESULT 8

GENE EXPRESSION LEVEL ANALYZING METHOD, GENE EXPRESSION LEVEL ANLAYZING PROGRAM, AND GENE EXPRESSION LEVEL ANALYZING DEVICE

BACKGROUND OF THE INVENTION

1. Technical Field

The present invention relates to a technical field associated with a gene expression level obtained using a bioassay bed.

2. Related Art

In the past, a technique was used which measures a quantity of complementary strands formed by plural designed DNA probes and cDNA into which mRNA extracted from a sample cell is converted with reverse transcriptase by the use of fluorescent intensity and which detects the gene expression level expressed in the sample cell from the measurement result.

The gene expression level varies with external factors such as external stress on the sample cell as an extraction target or differences in condition or skill at the time of the extraction of the mRNA from the sample cell. Therefore, it is of vital interest to know whether the gene expression level is reliable.

In general, when temporal changes in gene expression level are analyzed, attention is paid to an increasing gene expression level or a gene expression level with a high value, but a decreasing gene expression level or a gene expression level with a low value is discarded (for example, see Ido Amit, Ami Citri, Tal Shay, and others, A module of negative feedback regulators defines growth factor signaling, NATURE GENETICS, VOLUME 39, NUMBER 4, APRIL, 2007, p. 503-512).

SUMMARY OF THE INVENTION

However, a gene expression level to be decreased as a discard target or a gene expression level with a low value is an important factor for biologically precise examination. Therefore, when it can be determined whether a gene expression level of a low band generally considered to be discarded is reliable, it can be expected to help improve precision in analyzing gene expression levels.

Therefore, there is a need for a gene expression level analyzing method, a gene expression level analyzing program, and a gene expression level analyzing device capable of improving precision.

According to an embodiment of the invention, there is provided a gene expression level analyzing method including the steps of: acquiring expression levels of a plurality of target genes in a target cell every measurement time; extracting a maximum expression level and a minimum expression level from the expression levels of the target genes every measurement time; calculating a correlation coefficient of the frequency distribution of the gene having the maximum expression level at each measurement time and the frequency distribution of the gene having the minimum expression level at each measurement time; and comparing the correlation coefficient with a threshold value of the correlation coefficient.

According to another embodiment of the invention, there is provided a gene expression level analyzing program: allowing storage means to store data representing expression levels of a plurality of target genes in a target cell every measurement time; allowing arithmetic means to extract a maximum expression level and a minimum expression level from the expression levels of the target genes every measurement time; allowing the arithmetic means to calculate a correlation coefficient of the frequency distribution of the gene having the maximum expression level at each measurement time and the frequency distribution of the gene having the minimum expression level at each measurement time; and allowing the arithmetic means to compare the correlation coefficient with a threshold value of the correlation coefficient.

According to still another embodiment of the invention, there is provided a gene expression level analyzing device including: acquisition means for acquiring expression levels of a plurality of target genes in a target cell every measurement time; calculation means for extracting a maximum expression level and a minimum expression level from the expression levels of the target genes every measurement time and for calculating correlation coefficient of a frequency distribution of the gene having the maximum expression level at each measurement time and a frequency distribution of the gene having the minimum expression level at each measurement time; and comparison means for comparing the correlation coefficient with a threshold value of the correlation coefficient.

The applicant found that, among the gene expression levels in a cell, the gene with the minimum expression level at a certain measurement time and the gene with the maximum expression level at the same time have an excellent correlation every measurement time. It is thought this is because substances existing in a cell tend to stay constant and thus the total gene expression levels tend to stay substantially constant.

Therefore, the correlation coefficient calculated in the embodiment of the invention exhibits a higher value as an influence of a change resulting from a condition of an external stress on the target cell or differences in condition or skill at the time of extracting the mRNA from the target cell. In the embodiment of the invention, since the correlation coefficient is compared with the threshold value of the correlation coefficient, it is possible to determine the reliability with high precision of the gene expression levels of a gene group with a tendency to decrease or with a low value, which would generally be considered of doubtful reliability, as well as a gene group with a tendency to increase or with a high value which would be considered reliable.

According to the embodiments of the invention, since the reliability of the gene expression levels of a gene group with a tendency to decrease or with a low value, which would generally be considered to of doubtful reliability, can be determined, it is possible to further multilaterally analyze the gene expression levels.

BRIEF DESCRIPTION OF THE DRAWINGS

FIG. 5 is a diagram schematically illustrating the extraction of maximum and minimum expression levels of respective genes.

FIGS. 7A to 7D are graphs illustrating test result 2.

FIGS. 9A to 9F are graphs illustrating test result 4.

FIGS. 11A and 11B are diagrams schematically illustrating the conversion of the expression level of each gene into a ratio to create a reference for the expression level of the gene.

FIGS. 12A and 12B are diagrams schematically illustrating the extraction of the expression level ratios that represent the maximum and the minimum of each gene.

FIGS. 13A to 13F are graphs illustrating test result 5.

FIGS. 14A to 14F are graphs illustrating test result 6.

FIGS. 15A to 15H are graphs illustrating test result 7.

FIGS. 16A to 16H are graphs illustrating test result 8.

DESCRIPTION OF THE PREFERRED EMBODIMENTS

Hereinafter, an embodiment of the invention will be described in detail with reference to the accompanying drawings.

(1) Entire Configuration of Measurement System

Figure 1:
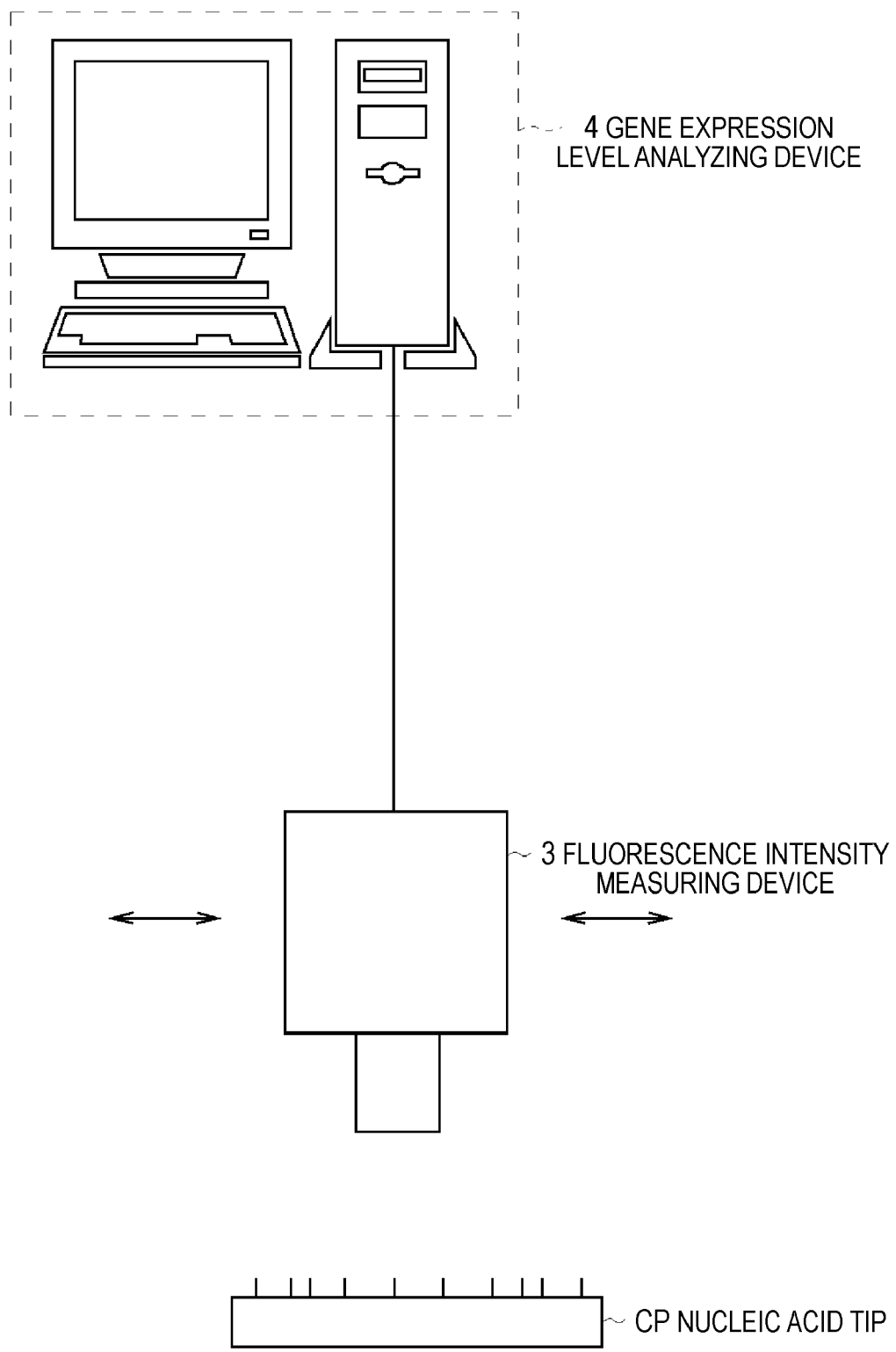
FIG. 1 is a diagram schematically illustrating the entire configuration of a measurement system according to an embodiment of the invention.

FIG. 1 shows the entire configuration of a measurement system 1 according to an embodiment of the invention. The measurement system 1 includes a fluorescence intensity measuring device 3 and a gene expression level analyzing device 4.

The fluorescence intensity measuring device 3 includes a measurement stage and a nucleic acid tip CP is set on the measurement stage. The nucleic acid tip CP is a bed on which nucleic acid probes corresponding to all genes in a target cell are arranged.

Figure 2:
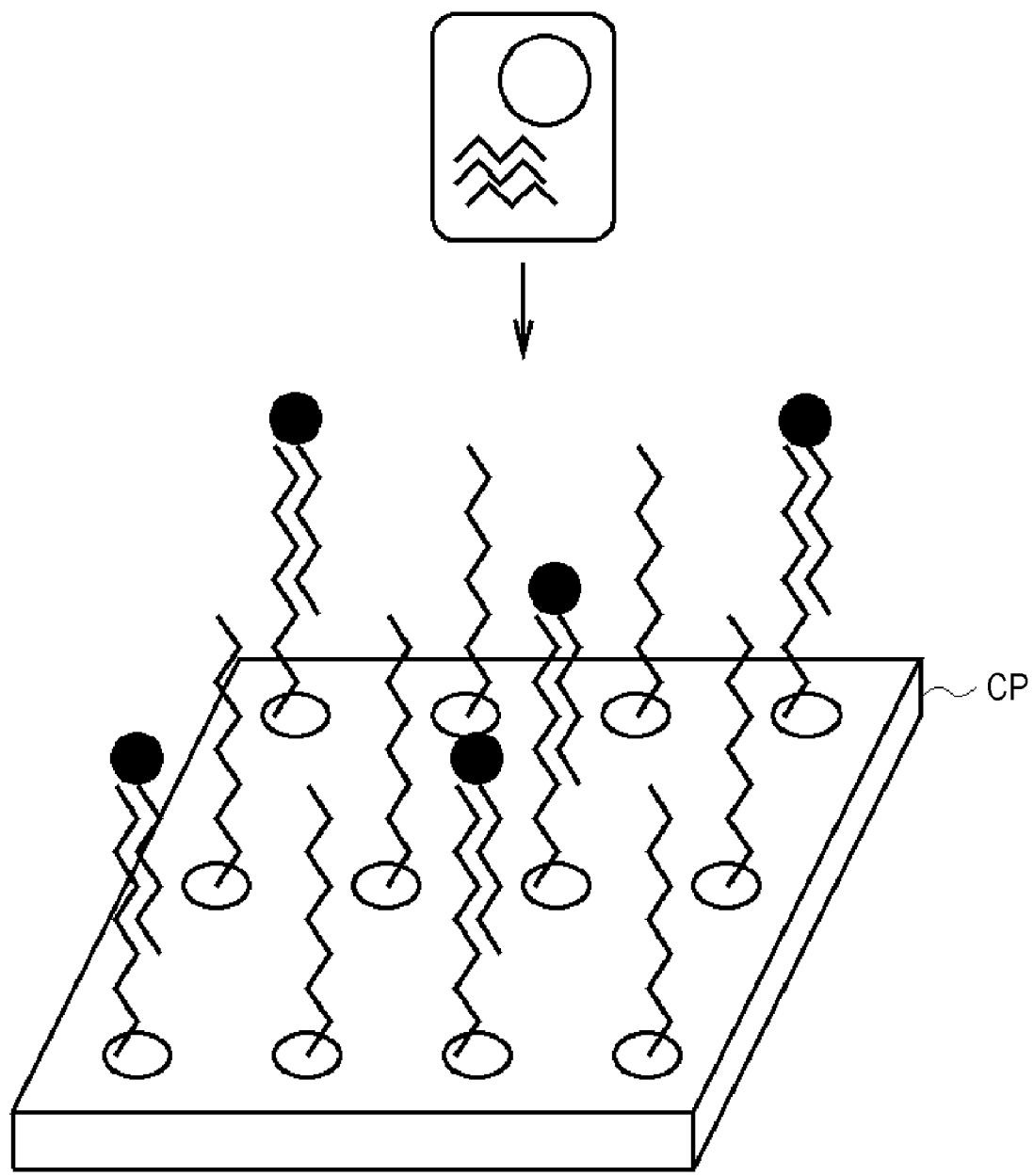
FIG. 2 is a diagram schematically illustrating hybridization in a nucleic acid tip.

In the nucleic acid tip CP, for example, as shown in FIG. 2, target nucleic acids (portions indicated by short waved lines) which are extracted from the cells of a target organism and to which labeled substances (portions indicated by black circles) are added are assigned to nucleic acid probes (portions indicated by long waved lines) and a complementary strand forming reaction (hereinafter, referred to as "hybridization") is performed on them.

The nucleic acid probes are generally designed as nucleotide fragments (hereinafter, referred to as "probe set") paired in plural base sequence portions specific to a corresponding gene and not as nucleotides paired in overall base sequences in the specific gene. Controls of the probe sets are also designed. The probe sets and the controls are arranged to form pairs in a predetermined region assigned to the nucleic acid tip CP. In addition, specifically, DNA (Deoxyribonucleic Acid) fragments, cDNA (Complementary DNA), or PNA (Peptide Nucleic Acid) of about 18 to 60 [mer] are used as the probe fragments.

A target nucleic acid is a single-strand nucleotide to be hybridized with a nucleic acid probe. In general, mRNA (including pre-mRNA) or its fragment is not used itself as the target nucleic acid, but the resultant into which the mRNA or its fragment is converted with reverse transcriptase is used.

The labeled substance is generally a fluorescent dye such as biotin or FITC (Fluorescein Isothiocyanate). However, the labeled substance is not limited to the fluorescent dye, for example, a radioactive isotope may be employed.

When a measurement instruction is given, the fluorescence intensity measuring device 3 (see FIG. 1) applies excited light of the labeled substance added to the target nucleic acid to the nucleic acid tip CP set on the measurement stage. When the nucleic acid probes being arranged in the nucleic acid tip CP and corresponding to genes form complementary strands with the target nucleic acids, the labeled substance added to the target nucleic acids emits light with the excited light. The emission intensity is related to the amount of complementary strands formed by the target nucleic acids and the nucleic acid probes. That is, as the amount of the target nucleic acids forming complementary strands with the nucleic acid probes increases, the emission intensity also increases.

The fluorescence intensity measuring device 3 measures the emission intensity of the nucleic acid probes and the controls after applying the excited light and produces measured emission intensity EM data (hereinafter, referred to as "fluorescence intensity data").

Figure 3:
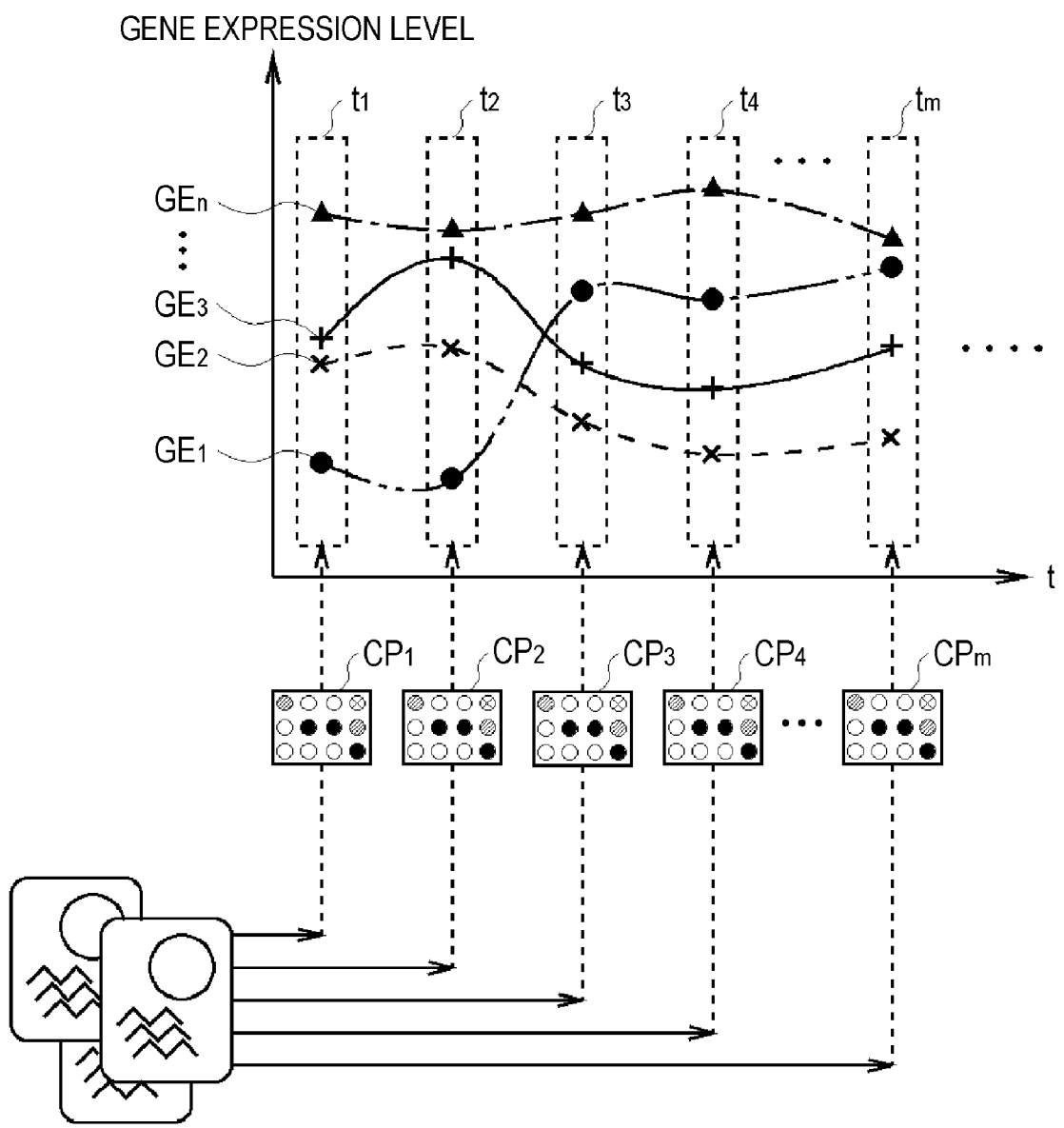
FIG. 3 is a diagram schematically illustrating acquisition of gene expression levels in a target cell every measurement time.

For example, as shown in FIG. 3, the gene expression level analyzing device 4 acquires expression levels $GE_n$ of genes $G_n$ (where n is a natural number) in cells of the target organism every measurement time $t_m$ (where m is a natural number) from the hybridization result of the target nucleic acids extracted from continuously-cultivated target cells every predetermined period and the nucleic acid probes in another nucleic acid tip CP with the same product number.

The gene expression level analyzing device 4 calculates a value (hereinafter, also referred to as "reliability index") from the gene expression levels $GE_n$ representing the degree of reliability of the gene expression levels. When the calculation result is equal to or greater than a threshold value for the reliability index, the acquired gene expression levels $GE_n$ are treated as useful information.

(2) Circuit Configuration of Gene Expression Level Analyzing Device

Figure 4:
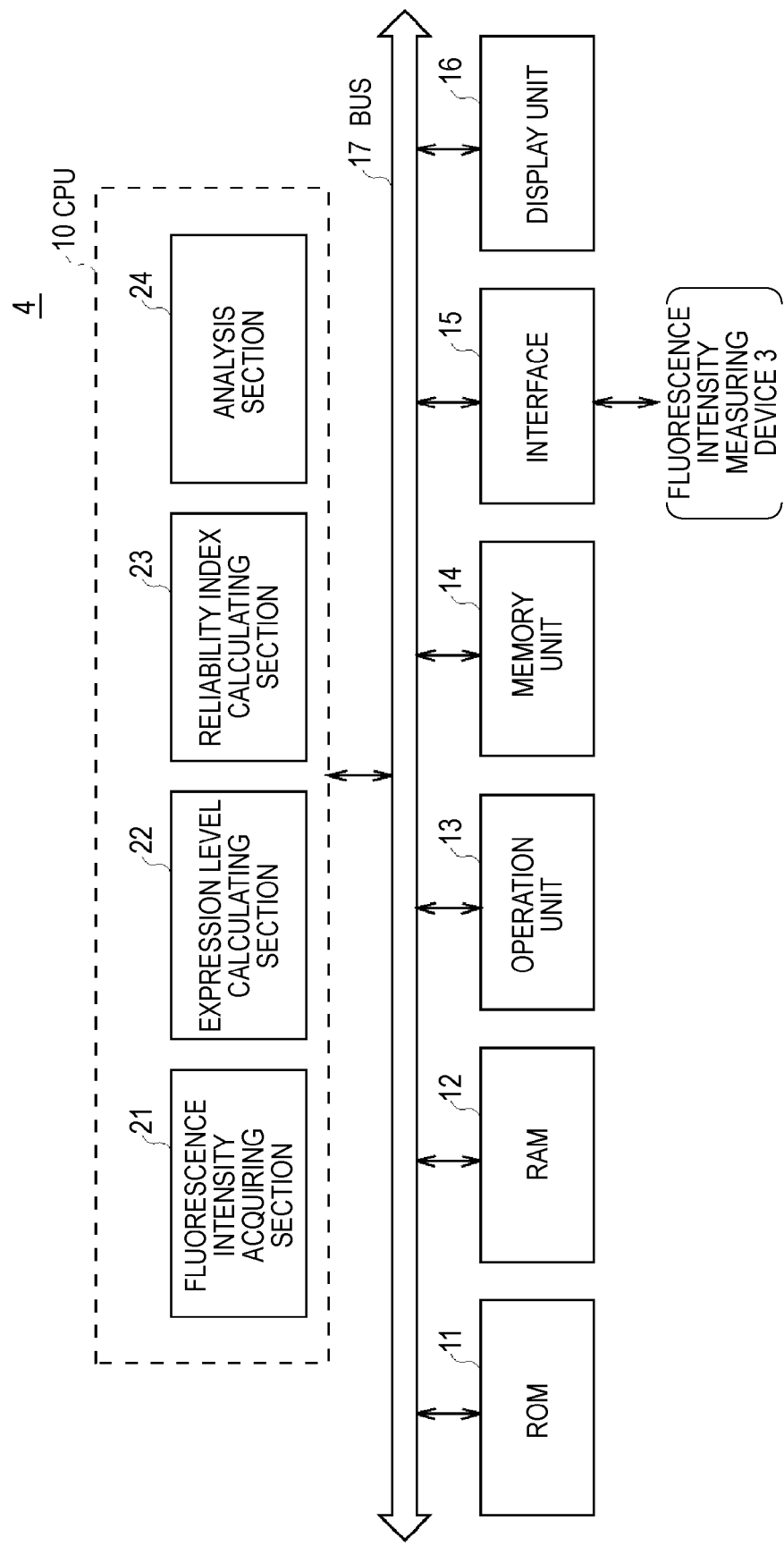
FIG. 4 is a block diagram illustrating a circuit configuration of a gene expression level analyzing device.

The configuration of the gene expression level analyzing device 4 will be described now. The gene expression level analyzing device 4 is constructed, as shown in FIG. 4, by connecting a variety of hardware to a CPU (Central Processing Unit) 10 which has overall control of gene expression level analyzing device 4.

Specifically, for example, a ROM (Read Only Memory) 11, a RAM (Random Access Memory) 12 which serves as the work memory of the CPU 10, an operation unit 13, a memory unit 14, an interface 15, and a display unit 16 are connected via a bus 17.

A program (hereinafter, also referred to as "gene expression level analyzing program") for executing a gene expression level analyzing process is stored in the ROM 11. The interface 15 can access the fluorescence intensity measuring device 3 in a wired or wireless manner.

When the gene expression level analyzing program stored in the ROM 11 is developed in the RAM 12, the CPU 10 properly controls the memory unit 14, the interface 15, and the display unit 16 on the basis of the gene expression level analyzing program in order to perform the gene expression level analyzing process.

(3) Processing Details of CPU Based on Gene Expression Level Analyzing Program

The CPU 10, having developed the gene expression level analyzing program in the RAM, can be functionally divided into a fluorescence intensity acquiring section 21, an expression level calculating section 22, a reliability index calculating section 23, and an analysis section 24, as shown in FIG. 4.

The fluorescence intensity acquiring section 21 waits for a fluorescence intensity measurement request on a nucleic acid tip $CP_i$ from the operation unit 13 and then requests fluorescence intensity measuring device 3 which is connected to the interface 15 for the measurement through the interface 15 when receiving the measurement request.

The fluorescence intensity acquiring section 21 generates, for example, the date and time of acquisition and the acquisition number as identifier data for the nucleic acid tip $CP_i$ (hereinafter, referred to as "tip identification data") when acquiring the fluorescence intensity from the fluorescence intensity measuring device 3 in response to the measurement request.

When the fluorescence intensity acquiring section 21 acquires the fluorescence intensity data, the expression level calculating section 22 calculates the gene expression level of each probe set on the basis of the fluorescence intensity data, correlates the data (hereinafter, referred to as "expression level data") representing the calculated expression level of each probe set with the tip identification data, and stores the resultant data in the memory unit 14.

The gene expression level is an estimated level representing a gene expressed in the target cell and is calculated as an emission intensity ratio using the emission intensity correlated with the amount of complementary strands formed by the target nucleic acids and the nucleic acid probes.

In this embodiment, the gene expression level is calculated using version 5 of data analysis software called MAS (Micro Array Suite) made by Affymetrix Inc.

Here, MAS5 will be described in brief with attention to a single probe set. In MAS5, (1) a local physical influence (background) is excluded from the emission intensity of each probe fragment in the probe set, (2) the emission intensity of each probe fragment (referred to as "perfect match probe") is suitably corrected depending on the difference with the fragment control (referred to as "mismatch probe") corresponding to the probe fragment, and (3) the emission intensity of each probe fragment (referred to as "perfect match probe") is calculated as a gene expression level by algebraic conversion.

Specifically, this process is referred to in "Micro Array Data Analysis for Combined Genomics," written by I. S. Kohane/A. T. Kho/A. J. Butte, and Hosida Yujin and published by Springer Japan, p. 58-74.

The reliability index calculating section 23 waits for a reliability index calculation start request from the operation unit 13 and determines whether two or more tip identification data (expression level data) are stored in the memory unit 14 when the calculation start request is received.

Here, when two or more tip identification data are not stored in the memory unit 14, it means that the gene expression level, which is necessary for calculating the reliability index, of the same target cell as a comparison opposite has not been acquired. In this case, the reliability index calculating section 23 displays a notification that the reliability index cannot be calculated and the reason thereof, for example, on the display unit 16.

When two or more tip identification data are stored in the memory unit 14, the reliability index calculating section 23 calculates the reliability index using all the tip identification data stored in the memory unit 14 and the expression level data correlated with the tip identification data.

That is, the reliability index calculating section 23 extracts the maximum gene expression level (hereinafter, also referred to as "maximum gene expression level") $GE_{nMAX}$ and the minimum gene expression level (hereinafter, also referred to as "minimum gene expression level") $GE_{nMIN}$ from the gene expression levels GE at all the measurement times $t_{1-m}$ for each gene, for example, as shown in FIG. 5.

Figure 6A:
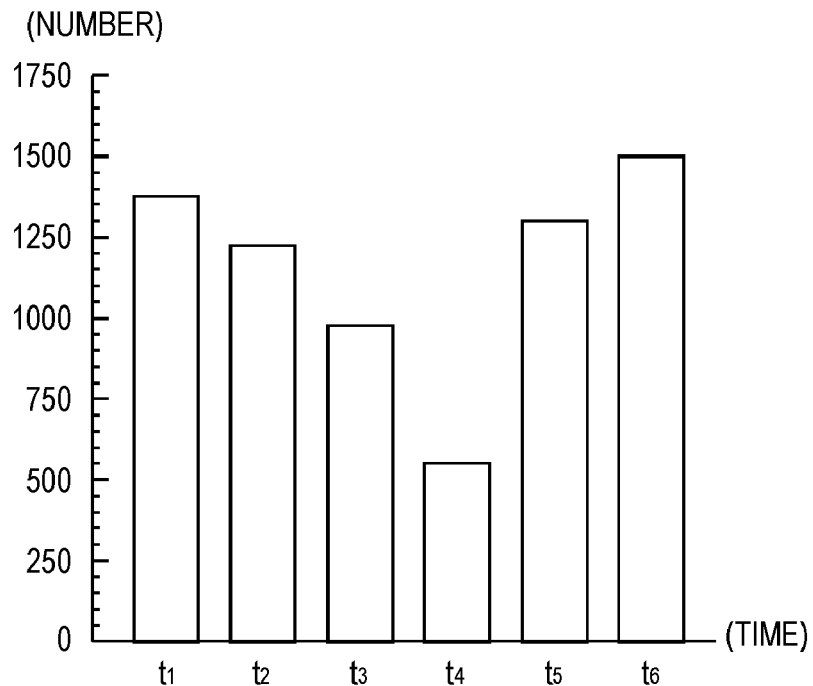
FIGS. 6A and 6B are graphs illustrating test result 1.
Figure 6B:
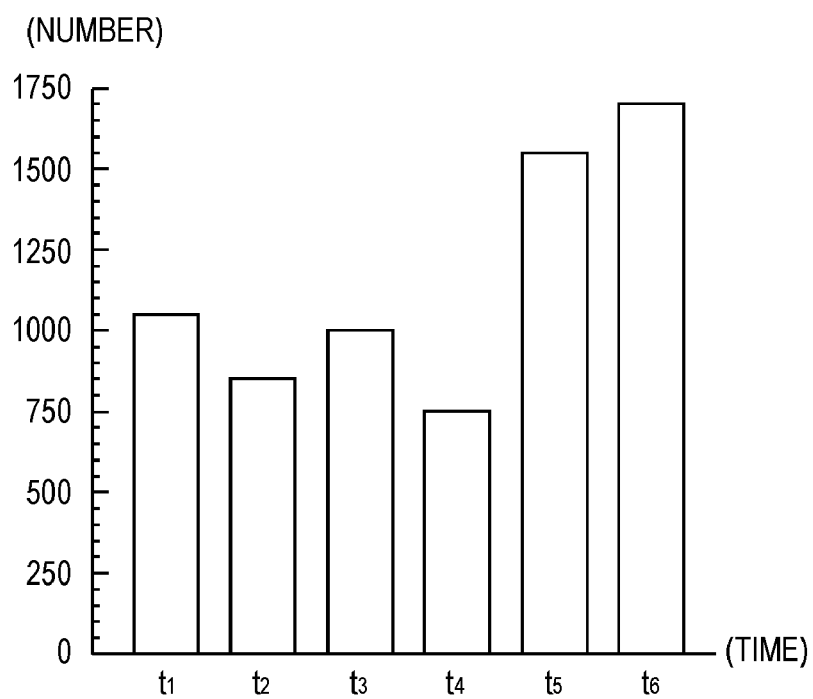
Figure 8C:
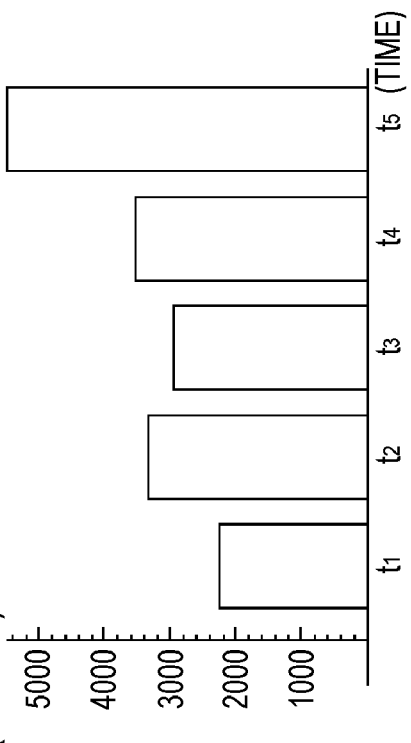
FIGS. 8A to 8D are graphs illustrating test result 3.
Figure 8D:
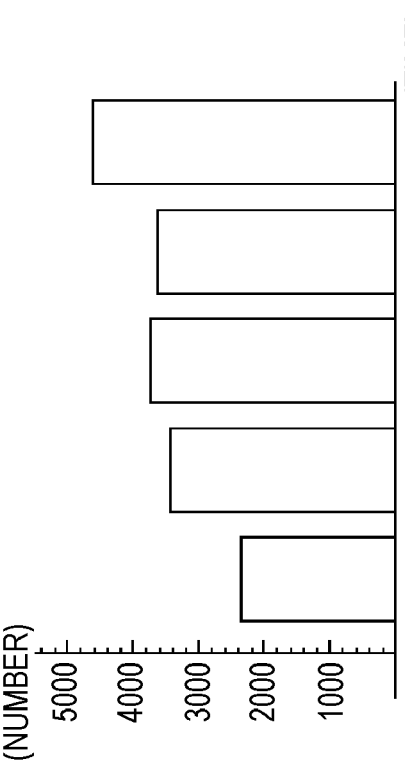
Figure 8A:
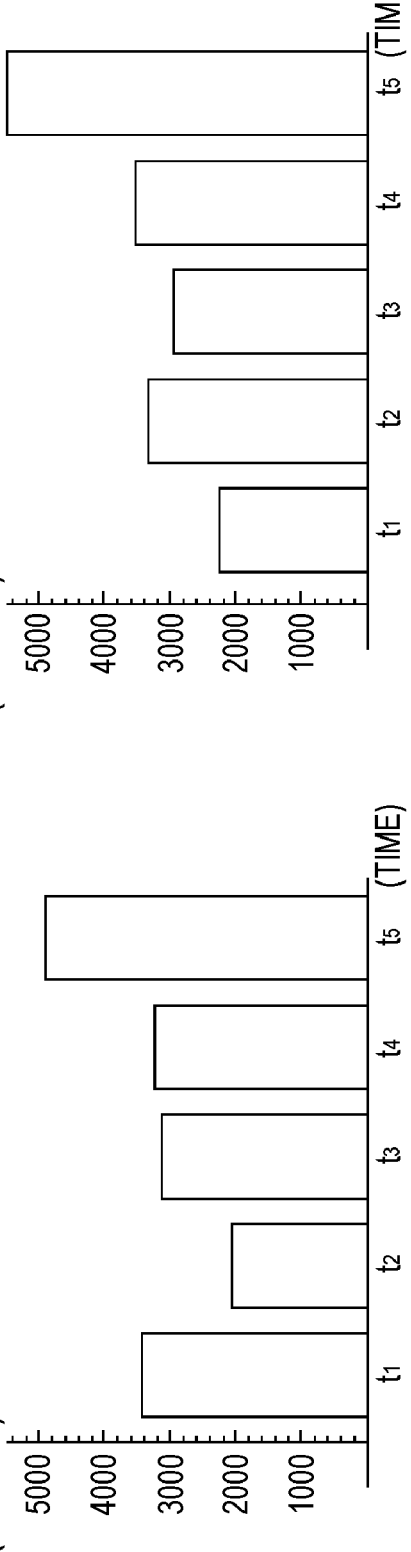
Figure 8B:
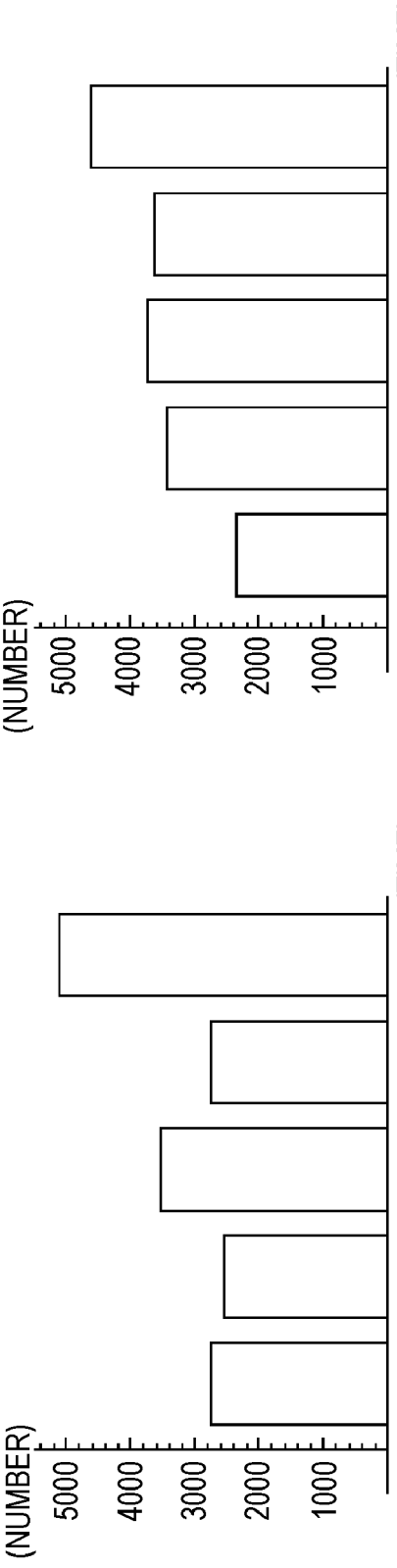

The reliability index calculating section 23 calculates as the reliability index a correlation coefficient of a frequency distribution (see FIG. 6A) of genes having the maximum gene expression level $GE_{nMAX}$ at the respective measurement times $t_m$ and a frequency distribution (see FIG. 6B) of genes having the minimum gene expression level $GE_{nMIN}$ at the respective measurement time $t_m$, for example, as shown in FIGS. 6A and 6B.

FIGS. 6A and 6B show the frequency distribution of genes having the maximum gene expression level $GE_{nMAX}$ at each measurement time $t_m$ and the frequency distribution of genes having the minimum gene expression level $GE_{nMIN}$ at the measurement time $t_m$, where E-GEOD-6013 is used as a sample and hemin is given to A549 cell as a stimulus. The measurement times $t_1$ to $t_6$ in FIGS. 6A and 6B are 0, 1, 6, 24, 48 [hours], and 7 [days], respectively.

It is generally known that various substances in a cell stay constant (homeostasis). It is also known that, CTP, GTP, and UTP which serve as constituent materials of mRNA, stay constant in tune with the amount of ATP (adenosine triphosphate) in a cell (for an example, see Faziol I. Ataullakhanov & Victor M. Vitvitsky, What determines the intracellular ATP concentration, Bioscience Reports vol. 22, Nos 5 & 6, October & December 2002, p. 501-p. 511).

It can be deduced from this knowledge that the total of the gene expression levels stays substantially constant even when the gene expression levels of the respective genes expressed in the cell are changed. Therefore, the change in maximum gene expression level $GE_{nMAX}$ and the change in minimum gene expression level $GE_{nMIN}$ at each measurement time $t_m$ tend to undergo transitions while maintaining a constant relationship. This has been confirmed already by the present applicant.

Here, test results other than those shown in FIGS. 6A and 6B are shown in FIGS. 7A to 7D, 8A to 8D, and 9A to 9F. FIGS. 7A to 7D show the frequency distribution (FIG. 7A) of genes having the maximum gene expression level $GE_{nMAX}$, the frequency distribution (FIG. 7B) of genes having the minimum gene expression level $GE_{nMIN}$ at each measurement time $t_m$, where E-GEOD-6013 is used as a sample and asbestos is given to A549 cell as a stimulus, and the frequency distribution (FIG. 7C) of genes having the maximum gene expression level $GE_{nMAX}$ and the frequency distribution (FIG. 7D) of genes having the minimum gene expression level $GE_{nMIN}$ at each measurement time $t_m$, where no stimulus is given to the A549 cell. The measurement times $t_1$ to $t_6$ in FIGS. 7A to 7D are the same as shown in FIGS. 6A and 6B.

FIGS. 8A to 8D show the frequency distribution (FIG. 8A) of genes having the maximum gene expression level $GE_{nMAX}$, the frequency distribution (FIG. 8B) of genes having the minimum gene expression level $GE_{nMIN}$ at each measurement time $t_m$, where E-GEOD-6013 is used as a sample and asbestos is given to Beas2B cell as a stimulus, and the frequency distribution (FIG. 8C) of genes having the maximum gene expression level $GE_{nMAX}$ and the frequency distribution (FIG. 8D) of genes having the minimum gene expression level $GE_{nMIN}$ at each measurement time $t_m$, where no stimulus is given to the Beas2B cell. The measurement times $t_1$ to $t_5$ in FIGS. 8A to 8D are 0, 1, 6, 24, and 48 [hours], respectively.

FIGS. 9A to 9F show the frequency distributions (FIGS. 9A, 9C, and 9E) of genes having the maximum gene expression level $GE_{nMAX}$ and the frequency distributions (FIGS. 9B, 9D, and 9F) of genes having the minimum gene expression level $GE_{nMIN}$ in three-person human bronchial epithelial cells at each measurement time $t_m$, where E-GEOD-5264 is used as a sample. The measurement times $t_1$ to $t_8$ in FIGS. 9A and 9B are 0, 1, 4, 8, 10, 14, 21, and 28 [days], respectively, the measurement times $t_1$ to $t_9$ in FIGS. 9C and 9D are 0, 4, 8, 10, 12, 14, 17, 21, and 28 [days], respectively, and the measurement times $t_1$ to $t_{11}$ in FIGS. 9E and 9F are 0, 1, 2, 4, 8, 10, 12, 14, 17, 21, and 28 [days], respectively.

As clearly shown by the test results, the change in maximum gene expression level $GE_{nMAX}$ and the change in minimum gene expression level $GE_{nMIN}$ at each measurement time $t_m$ transition while maintaining a constant relationship.

Therefore, when the correlation coefficient (reliability index) calculated by reliability index calculation section 23 is equal to or greater than a threshold value of the correlation coefficient, it means that as the gene expression level changes while maintaining a substantially constant relationship, changes resulting from external factors such as external stress on the target cell or differences in condition or skill at the time of mRNA extraction from the target cell are small in the gene expression level maintaining the relationship and the gene expression level is a true value equal to the real quantity of the gene in the target cell.

The analysis section 24 compares the correlation coefficient (reliability index) calculated by the reliability index calculating section 23 using the threshold value and determines that the data reliability of the expression level data stored in the memory unit 14 is high when the correlation coefficient is equal to or greater than the threshold value. The analysis section 24 adds to the expression level data an identifier stating the reliability index calculated by the reliability index calculating section 23 satisfies the reference value.

When the data reliability is determined to be high, the analysis section 24 arbitrarily performs, for example, the process of preparing a graph representing the temporal change in each gene or other analysis processes and displays the analysis result on the display unit 16.

When the correlation coefficient (reliability index) calculated by the reliability index calculating section 23 is less than the threshold value, the analysis section 24 determines that the reliability of the expression level data stored in the memory unit 14 is low. Then, the analysis section 24 adds to the expression level data an identifier stating the reliability index calculated by the reliability index calculating section 23 does not satisfy the reference value.

When the data reliability is determined to be low, the analysis section 24 displays a notification to select whether the expression level data stored in the memory unit 14 should be discarded.

(4) Flow of Gene Expression Level Analyzing Process

Figure 10:
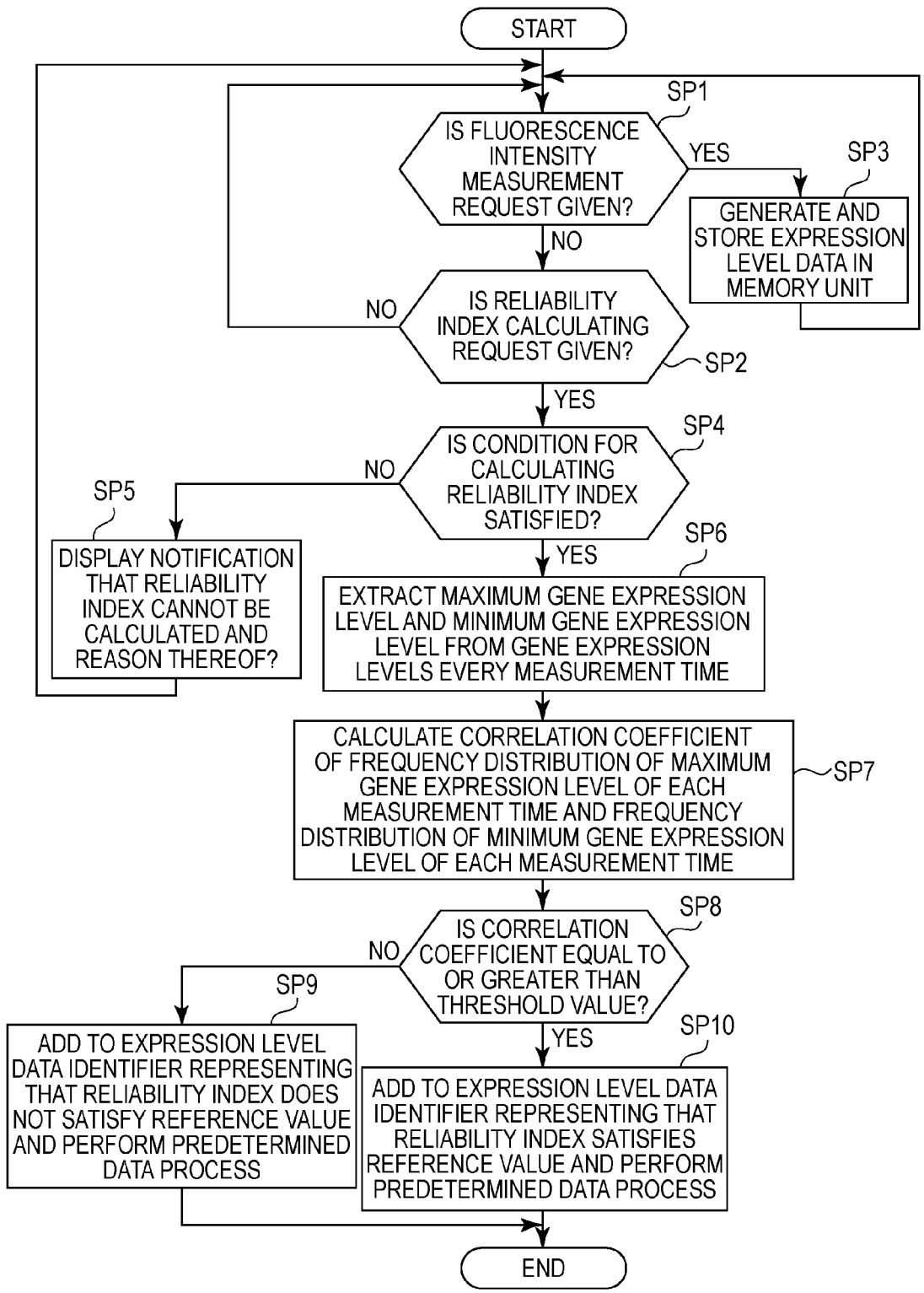
FIG. 10 is a flowchart illustrating the flow of a gene expression level analyzing process.

A process flow of the CPU based on the gene expression level analyzing program will be described now with reference to the flowchart shown in FIG. 10.

That is, the CPU 10 starts the flow of the gene expression analyzing process using, for example, a power-on operation as a trigger, waits for a fluorescence intensity measurement request in a nucleic acid tip CP in step SP1, and waits for a reliability index calculation start request in step SP2.

The CPU 10 instructs the fluorescence intensity measuring device 3 to start the measurement in step SP2 when a fluorescence intensity measurement request is received and acquires the fluorescence intensity data given by the fluorescence intensity measuring device 3 as the measurement result.

Then, the CPU 10 generates the expression level data representing the gene expression level from the fluorescence intensity data and stores the generated expression level data in the memory unit 14 in step SP3, then the CPU performs the process of step SP1 again.

When receiving the reliability index calculation start request, the CPU 10 determines whether the conditions for calculating the reliability index are satisfied on the basis of the data stored in the memory unit 14 in step SP4.

When two or more expression level data are not stored in the memory unit 14, the CPU 10 displays a notification that the reliability index cannot be calculated and the reason thereof in step SP5 and performs the process of SP1 again.

On the contrary, when two or more expression level data are stored in the memory unit 14, the CPU 10 extracts the maximum gene expression level $GE_{nMAX}$ and the minimum gene expression level $GE_{nMIN}$ from the gene expression levels $GE_n$ of each gene at the overall measurement times $t_{1-m}$ in step SP6 (see FIG. 5).

Subsequently, in step SP7, the CPU 10 calculates as the reliability index a correlation coefficient of the frequency distribution (FIG. 6A) of the gene having the maximum gene expression level $GE_{nMAX}$ at each measurement time $t_m$ and the frequency distribution (FIG. 6B) of the gene having the minimum gene expression level $GE_{nMIN}$ at the measurement time $t_m$ in step SP7 and compares the calculated correlation coefficient with the threshold value of the correlation coefficient in step SP8.

Here, when the correlation coefficient is less than the threshold value, it means that changes resulting from a condition of external stress on the target cell or differences in condition or skill at the time of the mRNA extraction from the target cell is great in the gene expression level and the gene expression level is a value apart from the real quantity of the gene in the target cell, as described above.

In this case, the CPU 10 determines that the data reliability of the expression level data stored in the memory unit 14 is low in step SP9. Then, the CPU 10 adds to the expression level data an identifier stating the reliability index does not satisfy the reference value, performs a data process prescribed as a process when the reliability index does not satisfy the reference value, and ends the gene expression level analyzing process.

On the contrary, when the correlation coefficient is equal to or greater than the threshold value, the CPU 10 determines that the data reliability of the expression level data stored in the memory unit 14 is high in step SP10. Then, the CPU 10 adds to the expression level data an identifier stating the reliability index satisfies the reference value, performs a data process prescribed as a process when the reliability index satisfies the reference value, and ends the gene expression level analyzing process.

In this way, the CPU 10 performs the gene expression level analyzing process on the basis of the gene expression level analyzing program.

(5) Operation and Advantage

In the above-mentioned configuration, the applicant found that the gene having the minimum expression level at a certain measurement time and the gene having the maximum expression level at the same measurement time have an excellent correlation every measurement time. This is because a substance included in a cell tends to stay constant and thus the total gene expression levels tend to stay substantially constant.

In general, when analyzing temporal change in gene expression level, attention is paid to the gene expression level to be increased or the gene expression level with a high value, but the gene expression level to be decreased or the gene expression level with a low value is discarded.

On the contrary, the gene expression level analyzing device 4 determines the reliability of the gene expression levels as a whole with a correlation coefficient of the gene expression levels that have been generally discarded and that have a low value and the gene expression level that have been given attention and that have a high value (FIGS. 5, 6A, and 6B).

Specifically, the maximum gene expression level $GE_{nMAX}$ and the minimum gene expression level $GE_{nMIN}$ are extracted from the gene expression levels $GE_n$ at the overall measurement times $t_{1-m}$ of every gene (FIG. 5), and it is determined that the gene expression levels $GE_n$ are high in reliability when the correlation coefficient of the frequency distribution (FIG. 6A) of the gene having the maximum gene expression level $GE_{nMAX}$ at each measurement time $t_m$ and the frequency distribution (FIG. 6B) of the gene having the minimum gene expression level $GE_{nMIN}$ at each measurement time $t_m$ is equal to or greater than the threshold value.

As described above, since the gene expression levels based on the homeostasis of a cell itself have a substantially constant correlation, the correlation coefficient exhibits a higher value as an influence of changes resulting from external stress on the target cell or a differences in condition or skill at the time of the mRNA extraction from the target cell is smaller.

Therefore, the gene expression level analyzing device 4 can determine the reliability of the gene expression level $GE_n$ with high precision. In addition, since the gene expression level analyzing device 4 can determine whether the gene expression levels of a gene group with a tendency to decrease or with a low value, which are generally considered to be of doubtful reliability, are reliable, it is possible to further multilaterally analyze the gene expression levels.

As the gene expression levels $GE_n$ get closer to the total number of genes which can be expressed in a target cell, the changes in the frequency distribution (FIG. 6A) of the gene having the maximum gene expression level $GE_{nMAX}$ and the frequency distribution (FIG. 6B) of the gene having the minimum gene expression level $GE_{nMIN}$ get finer. Accordingly, it is possible to determine the reliability with the highest precision.

Since the gene expression level analyzing device 4 acquires the correlation coefficient by calculation, it is possible to determine whether the reliability of the gene expression level $GE_n$ is higher without using a special control of the gene expression level $GE_n$ at each measurement time $t_m$.

Typically, a control serves as an indicator for a nucleic acid tip CP and does not serve as an indicator between the nucleic acid tips. Therefore, the control is also useful for analyzing a change in gene expression level in the same cell species of the same organism species using the expression level data acquired from different laboratories.

The gene expression level analyzing device 4 acquires the gene expression levels $GE_n$ using a statistical method of excluding a background (local physical influence) from a physical quantity (emission intensity in this embodiment) which is obtained by measuring a quantity of complementary strands formed by plural nucleic acid probes and target nucleic acids by the use of a sensor.

Therefore, since the gene expression level analyzing device 4 can calculate the correlation coefficient in a state where data serving as the basis for calculating the correlation coefficient gets closer to a true value, it is possible to better determine the reliability of the gene expression levels $GE_n$.

According to the above-mentioned configuration, it is possible to embody the gene expression level analyzing device 4 which is capable of improving the precision by determining the reliability of the gene expression levels $GE_n$ on the basis of the correlation coefficient of the frequency distribution (FIG. 6A) of the maximum gene expression level $GE_{nMAX}$ and the frequency distribution (FIG. 6B) of the minimum gene expression level $GE_{nMIN}$.

(6) OTHER EMBODIMENTS

In the above-mentioned embodiment, the correlation coefficient of the frequency distribution (FIG. 6A) of the gene having the maximum gene expression level $GE_{nMAX}$ at each measurement time $t_m$ and the frequency distribution (FIG. 6B) of the gene having the minimum gene expression level $GE_{nMIN}$ at the corresponding measurement time $t_m$ is calculated. This calculation method may be modified.

Specifically, as shown in FIGS. 11A and 11B, for example, a measurement time $t_1$ to be set as a reference is determined from the measurement times $t_m$ (FIG. 11A) and the gene expression levels $GE_n$ at the measurement times $t_m$ are converted into ratios to the gene expression level at the measurement time $t_1$ determined as the reference (FIG. 11B). By this conversion, it is possible to acquire a change ratio in the corresponding gene $G_n$ with respect to the initial gene expression level. In addition, the values of the gene expression levels $GE_n$ in FIGS. 11A and 11B are provided for the purpose of convenience but are not real numerical values.

As shown in FIGS. 12A and 12B, the maximum ratios (hatched portions in FIG. 12A) and the minimum ratios (horizontal-lined portions in FIG. 12B) from the ratios of the gene expression levels GE at the overall measurement times $t_{1-m}$ of each gene.

In this state, the correlation coefficient of the frequency distribution of the genes having the maximum ratios (right-left hatched portions in FIG. 12B) greater than a value (hereinafter, also referred to as "significantly-increasing border value") set greater than the reference ratio ("1") as a significantly-increasing border among the maximum ratios and the frequency distribution of the genes having the minimum ratios (vertical-horizontal lined portions in FIG. 12B) smaller than a value (hereinafter, also referred to as "significantly-decreasing border value") set smaller than the reference ratio as a significantly-decreasing border among the minimum ratios is calculated.

That is, the correlation coefficient can be obtained in a state where a gene group considered to have a small change relative to the reference (i.e. a gene group having a ratio equal to or less than the significantly-increasing border value and equal to or greater than the significantly-decreasing border value) is excluded. A gene group considered to have a small change relative to the reference has a relatively high dependency on the influence of change resulting from external stress on the target cell or differences in condition or skill at the time of mRNA extraction from the target cell.

Therefore, compared with the above-mentioned embodiment in which the correlation coefficient is calculated in a state where a gene group considered to have a small change relative to the reference is included, it is possible to determine the reliability of the gene expression levels $GE_n$ with higher precision.

Here, test results are shown in FIGS. 13A to 13F, 14A to 14F, 15A to 15H, and 16A to 16H. In FIGS. 13A to 13F, the gene distribution (FIGS. 13A, 13C, and 13E) having a maximum ratio greater than the significantly-increasing border value and the gene distribution (FIGS. 13B, 13D, and 13F) having a minimum ratio smaller than the significantly-decreasing border value are obtained using the gene expression levels in three-person human bronchial epithelial cells at each measurement time using E-GEOD-5264 as a sample. In this test, the significantly-increasing border value is "2" and the significantly-decreasing border value is "0.5". The measurement times in FIGS. 13A to 13F are the same as shown in FIGS. 9A to 9F. In addition, the measurement time $t_1$ (0 [hours]) is the reference (of which the ratio is "1") and this reference cannot have a maximum ratio greater than the significantly-increasing border value or a minimum ratio smaller than the significantly-decreasing border value and thus is not included in the distribution.

In FIGS. 14A to 14F, the gene distribution (FIGS. 14A, 14C, and 14E) having a maximum ratio greater than the significantly-increasing border value and the gene distribution (FIGS. 14B, 14D, and 14F) having a minimum ratio smaller than the significantly-decreasing border value are obtained under the same conditions as FIGS. 13A to 13F except for the significantly-increasing border value and the significantly-decreasing border value. In this test, the significantly-increasing border value is "1/0.7" and the significantly-decreasing border value is "0.7".

On the other hand, in FIGS. 15A to 15H, the gene distribution (FIGS. 15A, 15C, 15E, and 15G) having a maximum ratio greater than the significantly-increasing border value and the gene distribution (FIGS. 15B, 15D, 15F, and 15H) having a minimum ratio smaller than the significantly-decreasing border value are obtained using the gene expression levels in Beas2B cell and A549 cell at each measurement time and the gene expression levels at each measurement time when asbestos is given as a stimulus to the Beas2B cell and the A549 cell, where E-GEOD-6031 is used as a sample. In this test, the significantly-increasing border value is "2" and the significantly-decreasing border value is "0.5". The measurement times $t_2$ to $t_5$ in FIGS. 15A to 15D are the same as shown in FIGS. 8A to 8D and the measurement times $t_2$ to $t_6$ in FIGS. 15E to 15H are the same as FIGS. 7A to 7D.

In FIGS. 16A to 16H, the gene distribution (FIGS. 16A, 16C, 16E, and 16G) having a maximum ratio greater than the significantly-increasing border value and the gene distribution (FIGS. 16B, 16D, 16F, and 16H) having a minimum ratio smaller than the significantly-decreasing border value are obtained under the same conditions as FIGS. 12A and 12B except for the significantly-increasing border value and the significantly-decreasing border value. In this test, the significantly-increasing border value is "1/0.7" and the significantly-decreasing border value is "0.7".

As can be clearly seen from the test results, even when the number of gene distributions having the maximum ratio and the number of gene distributions having the minimum ratio (corresponding to the number of probes in the drawing) are different from each other, they have an excellent correlation. As can be seen from the comparison of FIGS. 13A to 13F with FIGS. 14A to 14F and the comparison of FIGS. 15A to 15H with FIGS. 16A to 16H, when the significantly-increasing border value is "1/0.7" and the significantly-decreasing border value is "0.7", the degree of correlation is the most excellent.

However, even when the significantly-increasing border value is a value other than "1/0.7" and the significantly-decreasing border value is a value other than "0.7", the applicant confirmed that no problem is caused substantially. The widths from the reference to the significantly-increasing border value and the significantly-decreasing border value are the same, but even when they are different, the applicant confirmed that no problem is caused substantially.

In the above-mentioned embodiment, as an example of acquiring the expression levels of plural target genes in a target cell at each measurement time, the gene expression levels $GE_n$ are acquired by calculation from the quantity of complementary strands formed by the nucleic acid probes and the plural target nucleic acids extracted from the target cell at each measurement time. However, the acquisition example is not limited to the above-mentioned embodiment. For example, the gene expression levels may be directly acquired by extracting the mRNAs expressed in the target cell and proliferating the mRNAs to a constant quantity using real-time PCR (Polymerase Chain Reaction).

For example, the gene expression level may be acquired from a data storage medium in which data representing the gene expression levels are stored. This example is useful for analyzing a change in gene expression level in the same or different cell species of the same organism species using the data representing the gene expression levels acquired from plural remote test locations.

Examples of the data storage medium include package mediums such as a flexible disk, a CD-ROM (Compact Disk-Read Only Memory), a DVD (Digital Versatile Disk) and a semiconductor memory or a magnetic disk in which data is temporally or permanently stored. In a method of acquiring data from the data storage medium, wired or wireless communication media such as a local area network, the Internet or a digital satellite broadcast may be used.

As the measured quantity, the emission intensity is optically measured in the above-mentioned embodiment. However, the measured quantity is not limited to that of the embodiment. For example, a quantity of electricity or impedance may be used electromagnetically. A quantity measured by a sensor for measuring a predetermined physical quantity may be used. For example, a Stanford type made by Affymetrix Inc. may be employed as the nucleic acid tip CP or others may be employed.

In the above-mentioned embodiment, the measurement location is the nucleic acid tip CP. However, the measurement location is not limited to the nucleic acid tip. For example, a tissue slice may be employed or other locations may be employed.

In the above-mentioned embodiment, the MAS is employed as the method of calculating the gene expression level. However, the calculation method is not limited to this method, but any method may be employed as long as it can properly correct, by the use of a statistical method, sensor-measured data representing the quantity of formed complementary strands.

The invention has applications in the field of biological industries such as gene testing, the creation and preparation of medicines, or patient follow-up.

The present application contains subject matter related to that disclosed in Japanese Priority Patent Application JP 2008-179255 filed in the Japan Patent Office on Jul. 9, 2008, the entire contents of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A gene expression level analyzing method comprising the steps of:
   acquiring, with a processor of an analyzing device, expression levels of a plurality of target genes in a target cell every measurement time;
   extracting, with the processor of the analyzing device, a maximum expression level and a minimum expression level from the expression levels of the target genes every measurement time;
   calculating, with the processor of the analyzing device, a correlation coefficient of a frequency distribution of target genes having the maximum expression level at each measurement time and a frequency distribution of target genes having the minimum expression level at each measurement time; and
   comparing, with the processor of the analyzing device, the correlation coefficient with a threshold value of the correlation coefficient.

2. The gene expression level analyzing method according to claim 1, further comprising the step of converting the expression level at each measurement time into a ratio to the expression level at a reference time, wherein:
the step of extracting the maximum expression level and the minimum expression level includes extracting a maximum ratio and a minimum ratio from the ratios of the expression levels at the measurement times for each target gene, and wherein the step of calculating the correlation coefficient includes calculating the correlation coefficient of the frequency distribution of target genes having a ratio higher than a value set higher than a reference ratio as a border significantly increasing among the maximum ratios at the measurement times and the frequency distribution of target genes having a ratio lower than a value set lower than a reference ratio as a border significantly decreasing among the minimum ratios at the measurement times.

3. The gene expression level analyzing method according to claim 2, wherein the step of acquiring the expression levels includes correcting a quantity of complementary strands formed by a plurality of target nucleic acids extracted from the target cell every measurement time and nucleic acid probes on the basis of differences of the nucleic acid probes from controls thereof and acquiring the expression levels.

4. The gene expression level analyzing method according to claim 3, wherein the step of acquiring the expression levels includes acquiring the expression levels of all the genes which can be expressed in the target cell every measurement time.

5. A machine-readable tangible and non-transitory medium having information for analyzing gene expression level recorded thereon, wherein the information, when read by the machine, causes the machine to perform the following:
storing data representing expression levels of a plurality of target genes in a target cell every measurement time;
extracting a maximum expression level and a minimum expression level from the expression levels of the target genes every measurement time;
calculating a correlation coefficient of a frequency distribution of target genes having the maximum expression level at each measurement time and a frequency distribution of target genes having the minimum expression level at each measurement time; and
comparing the correlation coefficient with a threshold value of the correlation coefficient.

6. A gene expression level analyzing device comprising:
acquisition means for acquiring expression levels of a plurality of target genes in a target cell every measurement time;
calculation means for extracting a maximum expression level and a minimum expression level from the expression levels of the target genes every measurement time and calculating a correlation coefficient of a frequency distribution of target genes having the maximum expression level at each measurement time and a frequency distribution of target genes having the minimum expression level at each measurement time; and
comparison means for comparing the correlation coefficient with a threshold value of the correlation coefficient.

7. A gene expression level analyzing device comprising:
an acquisition section configured to acquire expression levels of a plurality of target genes in a target cell every measurement time;
a calculation section configured to extract a maximum expression level and a minimum expression level from the expression levels of the target genes every measurement time and calculate a correlation coefficient of a frequency distribution of target genes having the maximum expression level at each measurement time and a frequency distribution of target genes having the minimum expression level at each measurement time; and
a comparison section configured to compare the correlation coefficient with a threshold value of the correlation coefficient.

* * * * *